United States Patent [19]

Hall

[11] 3,981,924

[45] Sept. 21, 1976

[54] DIELS-ALDER ADDUCT PRODUCT
[75] Inventor: John B. Hall, Rumson, N.J.
[73] Assignee: International Flavors & Fragrances Inc., New York, N.Y.
[22] Filed: June 26, 1975
[21] Appl. No.: 590,473

Related U.S. Application Data
[62] Division of Ser. No. 462,750, April 22, 1974, Pat. No. 3,929,895.

[52] U.S. Cl. .............................................. 260/598
[51] Int. Cl.² ........................................ C07C 47/45
[58] Field of Search .................................... 260/598

[56] References Cited
OTHER PUBLICATIONS
Arbuzov, Chem. Abs., vol. 29, (1936), p. 6888.

Primary Examiner—Bernard Helfin
Attorney, Agent, or Firm—Arthur L. Liberman; Harold Haidt

[57] ABSTRACT
A superatmospheric process for directly producing a Diels-Alder adduct which comprises admixing:
  i. A conjugated diene which can be either alpha-terpinene, allo-ocimene, cyclopentadiene or myrcene; with
  ii. A carbonyl group-containing compound which can be either acetone, acetaldehyde propionaldehyde or methylethyl ketone; with
  iii. An aldehyde source which can be either a formaldehyde source or an acetaldehyde source which aldehyde source will yield formaldehyde or acetaldehyde; in the presence of
  iv. A secondary amine catalyst such as a lower dialkyl amine or a cyclic amine such as morpholine, pyrrolidine or piperidine,
at a temperature in the range of from about 120° up to about 200°C for a period of time from about 2 hours up to about 8 hours, and novel products produced therefrom to wit:

i. A mixture of compounds having the structures:

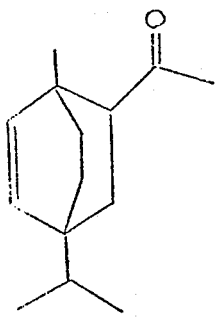

and 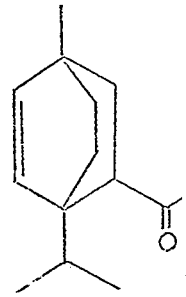

ii. A mixture of compounds having the structure:

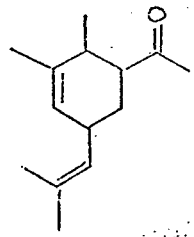

and 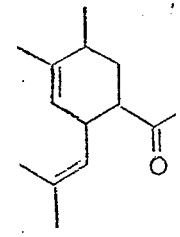

and
iii. and a mixture of compounds having the structures:

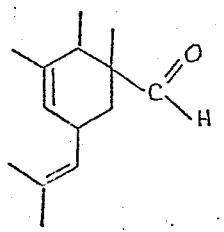

and

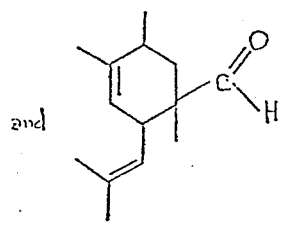

1 Claim, No Drawings

DIELS-ALDER ADDUCT PRODUCT

This application is a division of copending application for U.S. Letters Patent Ser. No. 462,750 filed on Apr. 22, 1974 and now U.S. Pat. No. 3,929,895 issued on Dec. 30, 1975.

BACKGROUND OF THE INVENTION

The present invention relates to processes for producing cycloalkenyl derivatives from the reaction of acrolein, methacrolein and alkyl vinyl ketone, all formed in situ, with conjugated dienes in good yields.

The Diels-Alder reaction is well known in the field of organic chemistry, and the classic example thereof is the reaction of a conjugated diene with a conjugated alkylene carbonyl compound to provide a cyclohexene derivative. Since the original reaction was set forth, there have been many variations of the reaction.

U.S. Pat. No. 3,341,601 issued on Sept. 12, 1967, relates to a process for producing Diels-Alder adducts of conjugated dienes and carbonyl compounds, wherein the adducts are produced by contacting a reaction mixture comprising a conjugated diene and a carbonyl compound having at least two alpha-hydrogen atoms with a condensation-dehydration catalyst at elevated temperatures according to the following reaction:

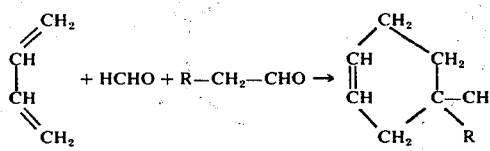

Although an in-situ formed methacrolein material is shown to be produced and act as a dienophile in the disclosure of U.S. Pat. No. 3,341,601, the dienes used in this reaction are relatively simple in nature.

Although the reaction of long chain aldehydes with formaldehyde in the presence of an amine catalyst is disclosed in U.S. Pat. No. 3,463,818, no suggestion of the carrying out of a Diels-Alder reaction is set forth therein. U.S. Pat. No. 3,463,818 relates to a process for producing alpha-methylene and alpha-methyl aldehydes and alcohols by reaction, in the presence of an amine catalyst, an aldehyde such as citronellal with formaldehyde.

U.S. Pat. No. 2,373,568 shows the Diels-Alder reaction of methacrolein and cyclopentadiene under pressure at about 140°C to provide a material with a camphoraceous aroma and the further reaction of the Diels-Alder product with acetone and sodium methylate to provide a product with a floral-type odor. Vaughan et al. in *J.A.C.S.* 74, 5355 shows the reaction of mesityl oxide and cyclopentadiene produced in situ by thermal depolymerization of the dimer to provide an unsaturated ketone by carrying out the reaction at 160°C for 12 hours to provide 21% yield, based upon mesityl oxide.

Chemical Abstracts 47, 12271e shows a diene condensation at 160°C in the presence of pyrolgallol.

Chemical Abstracts, Vol. 56, 4692c discloses the Diels-Alder reaction of allo-ocimene with appropriate carbonyl compounds such as acrylonitrile to yield naphthalene derivatives in the presence of hydroquinone at 160°–200°C for a period of time of from 2½ hours up to 6 hours in 50–71.5% yields.

Acrolein and allo-ocimene have been shown to react to form Diels-Alder adducts in the presence of hydroquinone by B. A. Arbuzov and A. R. Vil'chinskaya (State Univ., Kazan). Zhur. Obshchei Khim. 31, 2199-204 (1961).

A. R. Vil'chinskaya and B. A. Arbuzov, Voprosy Khim. Terpenov i Terpenoidov, Akad. Nauk Litovsk, S. S. R., Trudy Vsesoyuz, Soveshchaniya, Vil'nyus 1959, 201-7 (Pub. 1960) also show reaction products of crotonaldehyde with allo-ocimene (also see Vol. 55, Chemical Abstracts, 16495d). The Diels-Alder reaction of allo-ocimene with acrolein or crotonaldehyde is also set forth in Vol. 29, Chemical Abstracts 6888[6] (Abstract of Berichte 68B, 1435-8 (1935). Also suggested in the Berichte article is the condensation of the thus produced reaction products with acetone and other ketones to form "odoriferous ionone-like compounds". U.S. Pat. No. 3,067,244 discloses, interalia, the catalyzed condensation of cyclopentadiene with acrolein.

British Pat. No. 896,039 entitled "Method of Producing Derivatives of the 1,1-Dimethyl-Octahydronaphthalene Series" discloses the generic process:

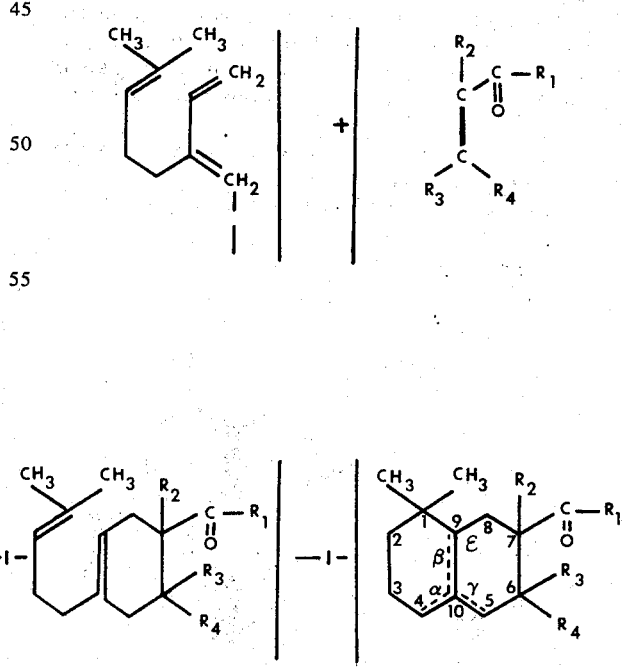

wherein $R_2$, $R_3$ and $R_4$ are disclosed to be same or different hydrogen atoms or alkyl and $R_1$ is disclosed to be hydroxy, alkyl or alkoxy. The British patent discloses this process to be useful for producing products "resembling the well known class of violet perfumes". Indeed, Example 5 of the British Patent alleges that the compound 1,1,6,6-tetramethyl-7-ketomethyl-octalin produced by (1) reacting myrcene and mesityl oxide thermally followed by (2) subsequent cyclization, has a pleasant "woody ambergris smell".

Further, cyclization reactions of Diels-Alder adducts of myrcene and a dienophile are set forth in U.S. Pat. No. 3,076,022. This patent discloses interalia, preparation of the thermal Diels-Alder adduct of myrcene and methyl isopropenyl ketone and subsequent acid cyclization to a product said to possess "an intense ambergris-like note".

Ohloff (Chemistry of Odoriferous and Flavoring Substances) pp. 185–240 (at page 192) Fortschritte & der Chemischen Forschung Vol. 12, Part 2, 1969, discloses a compound having the structure:

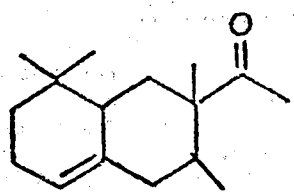

Ohloff indicates that materials of this nature have "resiny odors" like olebanum, with amber type undertones.

THE INVENTION

This invention relates to the preparation of synthetic woody or floral, melony, or green, woody, herbaceous or citrusy fragrance ingredients for perfumes and cosmetics and to certain novel mixtures produced by means of said preparation. More particularly, the invention has to do with a process for the preparation of floral, melony, or green, woody, herbaceous or citrusy fragrance compositions and intermediates used in the preparation of amber-like or fruity, or fruity-amber, or woody, or green, or yeasty, or buttery, or ionone-like or pineapple-like fragrance compositions for use in perfumery.

The novel mixtures which this invention covers are exemplified as follows:

i. mixture of compounds having the structures:

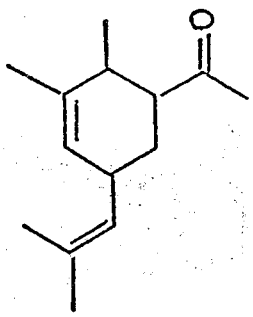 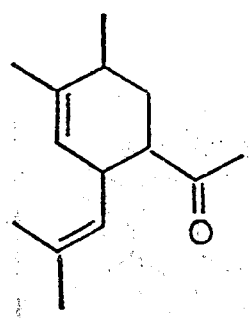

ii. mixture of compounds having the structures:

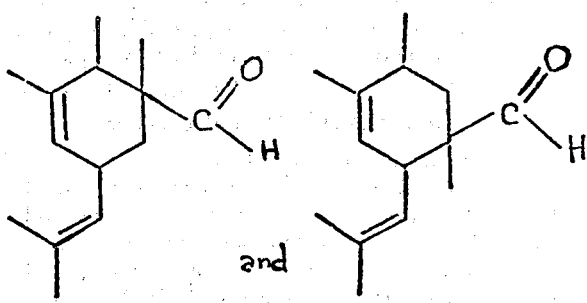

iii. and a mixture of compounds having the structures:

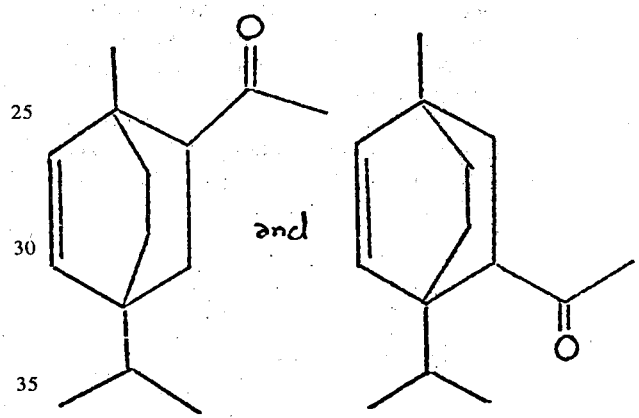

The invention also covers processes for producing, directly, Diels-Alder adducts which process comprises intimately admixing:
  i. A conjugated diene selected from the group consisting of alpha-terpinene, allo-ocimene, cyclopentadine and myrcene; with
  ii. a carbonyl group-containing compound selected from the group consisting of acetone, acetaldehyde, propionaldehyde and methyl-ethyl ketones; with
  iii. an aldehyde source selected from the group consisting of a formaldehyde source and an acetaldehyde source; and
  iv. a secondary amine catalyst.

A particular feature of my invention is that the dienophile (the condensation products which are obtained by the reaction of the carbonyl-group-containing compound and the aldehyde source) immediately reacts with the conjugated diene, thus forming the Diels-Alder adduct. The dienophiles may be considered as being acrolein, methacrolein, methyl vinyl ketone and 3-methyl pent-3-en-2-one. The decisive advantages of the instant process are:
  i. many low molecular weight substituted acroleins and alpha, beta-unsaturated ketones are skin, eye and respiratory irritants and therefore, at best, unpleasant to handle;
  ii. the great reactivity of acrolein, alpha-substituted acroleins and low molecular weight alpha-betaunsaturated ketones makes them unsuitable for storage without decomposition; and iii. more efficient processing is accomplished by combining the formation of the dienophile with the Diels-Alder reaction without having two separate reactions to carry out in a manufacturing operation.

The resulting adducts are useful per se as perfumery materials, having green floral odors or they may be further reacted as by cyclization as further exemplified herein to form other materials which are useful in perfumery for their amber-like or fruity or fruity-amber or woody, or green or yeasty or buttery or ionone-like or pineapple-like fragrances and which are useful in tobacco because they modify the aromas of the mainstream and sidestreams of a smoking article on smoking by imparting to the aroma of such mainstream and sidestream sweet, spicy, cedarwood-like notes.

The basic process of our invention involves heating a mixture of a conjugated diene with the carbonyl group-containing compound, and the aldehyde source, and a secondary amine catalyst in an autoclave at pressures substantially greater than atmospheric at temperatures in the range of 120° up to 200°C for a period of time of from 2 hours up to 8 hours.

The conjugated diene in our invention is specific and may be one of the following materials:
  i. alpha-terpinene;
  ii. allo-ocimene;
  iii. cyclopentadiene; or
  i. myrcene Myrcene is commercially available inpurities of 70% and upwards, and it can be used in this form. It is generally preferred in the practice of this invention to use commercial myrcene (approximately 72–77% purity), although, obviously, purified myrcene may be used. Such a purification is readily accomplished by fractional distillation.

The carbonyl group-containing compound is also specific in the process of our invention and may be either:
  i. acetone;
  ii. acetaldehyde;
  iii. propionaldehyde; or
  iv. methyl-ethyl ketone It is preferred that the purity of the aldehyde or ketone be between 90 and 100%; preferably as close to 100% as possible, in order to avoid purification problems at the end of the reaction.

The aldehyde source which is selected from the group consisting of a formaldehyde source and an acetaldehyde source may be one of the following materials:
  i. paraformaldehyde (a formaldehyde polymer of high molecular weight which depolymerizes at the reaction temperature);
  ii. formalin (a 40% solution of formaldehyde containing a small amount of methanol); or
  iii. acetaldehyde The catalyst used is a secondary amine, preferably diethyl amine or dimethyl amine which may be in the form of a salt of the amine with an inorganic acid such as dimethyl amine sulfate and diethyl amine sulfate. Other secondary amines which are suitable for the instant reaction are as follows:
  Methyl ethyl amine
  Methyl n-propyl amine
  Methyl isopropyl amine
  Ethyl isopropyl amine
  Ethyl n-butyl amine
  Ethyl t-butyl amine
  Pyrrolidine
  Piperidine
  Morpholine The amine catalyst may be introduced into the reaction mass as such, in the gaseous phase, or in solution, for example, in aqueous solution. The catalyst, when used as a salt, may be preformed or it may be formed in-situ in the reaction mass. Thus, for example, the secondary amine may be first introduced into the reaction mass, followed by the mineral acid which will form the amine salt.

Theoretically, the mole ratio of conjugated diene:carbonyl group-containing compound:aldehyde source is 1:1:1. Nevertheless, it is preferred to use a slight excess of aldehyde source with respect to carbonyl group-containing compound and conjugated diene. Also, it is preferred to use a slight molar excess of carbonyl group-containing compound with respect to conjugated diene. The mole ratio of secondary amine:conjugated diene is preferably between 1:20 and 1:5. Excess amine catalyst gives rise to problems concerning work-up after the completion of the reaction. Too little amine catalyst will cause the reaction to be inordinately slow, and therefore commercially impractical.

The reaction temperature can vary from 120° up to 200°C, with a temperature range of 150°–180°C being preferred. At lower temperatures longer reaction times are required. In view of the nature of the catalyst used, the temperature of 120°–200°C gives rise to the use of pressures higher than atmospheric. Accordingly, the use of pressure reaction vessels are required.

The order of addition of reactants and catalyst is not critical; however, it is preferred to pre-mix the conjugated diene, aldehyde source and carbonyl group-containing compound prior to addition of the secondary amine catalyst. Furthermore, it is preferred to pre-mix the secondary amine with the conjugated diene, carbonyl group-containing compound and aldehyde source prior to addition of the mineral acid (when desired) whereby the catalyst salt will be produced.

In carrying out the reaction, it is preferable to use an acid pH of between about 3 and about 6. Nevertheless, a pH of up to 8 will not be detrimental to the reaction.

The following table sets forth the type of reaction product which will be produced using the aforementioned reactants:

TABLE I
| Reactants<br>Conjugated Diene<br>Carbonyl Group-Containing Compound<br>Aldehyde Source | Structure(s) of Product(s) |
|---|---|
| myrcene<br>propionaldehyde<br>formalin | 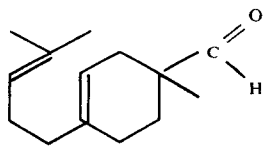<br>and<br>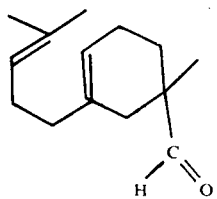 |
| Myrcene<br>Acetaldehyde<br>Formalin | 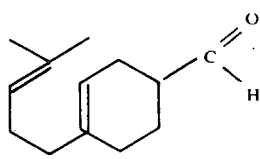<br>and<br>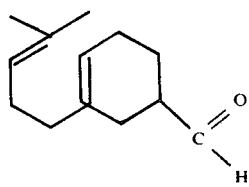 |
| Myrcene<br>Acetone<br>Formalin | 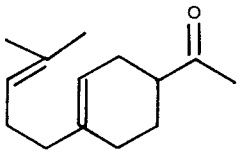<br>and<br>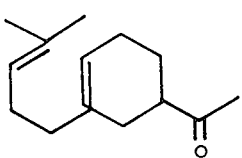 |

TABLE I-continued
| Reactants<br>Conjugated Diene<br>Carbonyl Group-Containing<br>Compound<br>Aldehyde Source | Structure(s) of Product(s) |
|---|---|
| Myrcene<br>Methyl-ethyl ketone<br>Acetaldehyde | 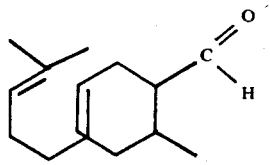<br><br>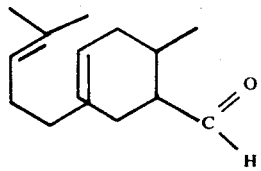<br><br>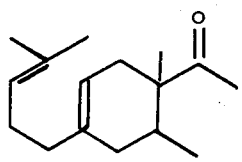<br><br>and<br><br>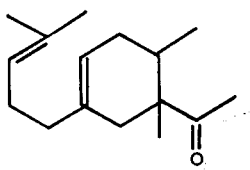 |
| Myrcene<br>Methylethyl ketone<br>Formalin | 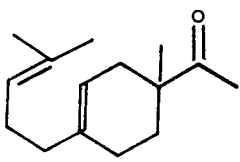<br><br>and<br><br>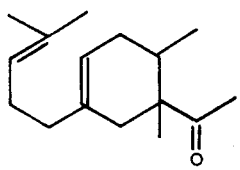 |

TABLE I-continued
| Reactants<br>Conjugated Diene<br>Carbonyl Group-Containing Compound<br>Aldehyde Source | Structure(s) of Product(s) |
|---|---|
| Cyclopentadiene<br>Propionaldehyde<br>Formalin |  |
| Allo-ocimene<br>Acetone<br>Formalin | 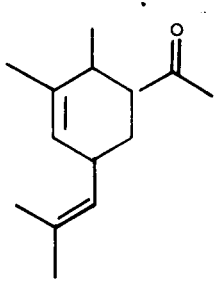<br>and<br>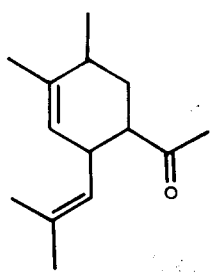 |
| Alpha-Terpinene<br>Acetone<br>Formalin | 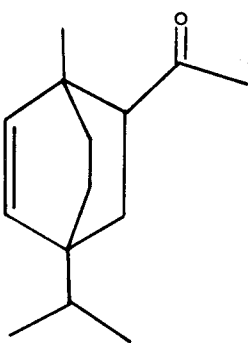<br>and<br>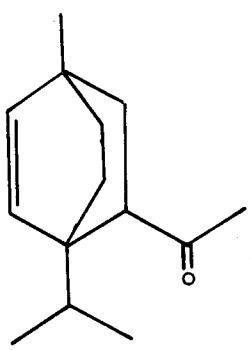 |

TABLE I-continued

| Reactants<br>Conjugated Diene<br>Carbonyl Group-Containing<br>Compound<br>Aldehyde Source | Structure(s) of Product(s) |
|---|---|
| Allo-ocimene<br>Propionaldehyde<br>Paraformaldehyde | 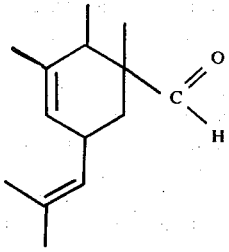<br>and<br>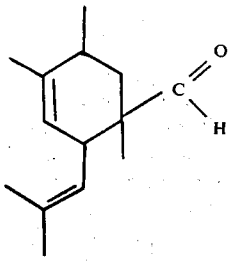 |

When the reaction is substantially complete, the reaction mass is then washed and the organic layer is separated and distilled.

The distilled product may be used "as is" in perfumery or it may be, in certain cases, further reacted, as by cyclization of the compound:

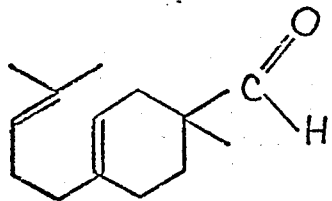

using concentrated phosphoric acid to form a compound having the structure:

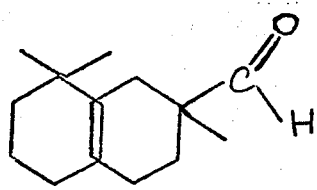

The novel mixtures of our invention have woody and woody, green, herbaceous aromas. A number of the products produced by our process which are not novel, have green, floral odors for use in such perfume compositions as rose, violet and lily-of-the valley. A number of intermediates prepared by the process of our invention when cyclyzed give rise to compounds having intense and persistent amber-like, fruity, or fruity amber or woody or green or yeasty or buttery or ionone-like or pineapple-like odors.

The products produced by the process of my invention, including my novel mixtures, and an auxiliary perfume ingredient including, for example, alcohols, aldehydes, nitriles, esters, cyclic esters and natural essential oils may be admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all states of evaporation and substances which retard evaporation; and (d) topnotes which are usually low boiling fresh smelling materials.

In perfume compositions, the individual component will contribute its particular olfactory characteristics but the over-all effect of the perfume composition will be the sum of the effects of each of the ingredients. Thus, the products produced by the process of my invention including my novel mixtures can be used to alter the aroma characteristics of a perfume composition, for example, by utilizing or moderating the olfactory reaction contributed by another ingredient in the composition.

The amount of the products produced by the process of my invention including my novel mixtures which will be effective in perfume compositions depend on many factors including the other ingredients, their amounts and the effects which are desired. It has been found that perfume compositions containing as little as 0.05% of the products produced by the process of my invention, including my novel mixtures, or even less can be used to impart an amber-like, fruity, or fruity amber or woody or green or yeasty or buttery or ionone-like or pineapple-like type scent odor to soaps, cosmetics and other products. The amount employed an range up to 5% of the fragrance components and will depend on considerations of cost, nature of the end product, the effect desired on the finished product and the particular fragrance sought.

The products produced by the process of my invention including my novel mixtures are useful in perfume compositions as olfactory components in detergents and soaps; space odorants and deodorants; perfumes; colognes; toilet water; bath preparations such as bath oils and bath solids; hair preparations such as lacquers, brilliantines, pomades and shampoo; cosmetic preparations such as creams, deodorants, hand lotions and sunscreens; powders such as talcs, dusting powders, face powders and the like. When used as an olfactory component of a perfumed article, as little as 100 parts per million of the products produced by the process of my invention, including my novel mixtures, will suffice to impart low keyed amber-like, fruity, or fruity-amber or woody or green or yeasty or buttery or ionone-like or pineapple-like characteristics. Generally, no more than 0.5% of the products produced by the process of my invention, including my novel mixtures based on the ultimate end product is required in the perfume composition.

In addition, the perfume composition or fragrance composition of this invention contain a vehicle or carrier for the products produced by the process of my invention, including my novel mixtures. The vehicle can be a liquid such as an alcohol, a non-toxic alcohol, a non-toxic glycol or the like. The carrier can also be an absorbent solid such as a gum (e.g., gum arabic) or components for encapsulating the composition (such as gelatine).

It will thus be apparent that the products produced by the process of my invention, including my novel mixtures, can be utilized to alter the sensory properties, particularly organoleptic properties such as flavor and/or fragrances of a wide variety of consumable materials.

In making the perfumes using the materials produced by the instant invention, such materials can be combined with "auxiliary perfume adjuvants", including one or more of many types of odor materials such as bergamot oil, vetiver oil, patchouli oil, sandalwood oil, oakmoss and floral musk. The materials produced according to this invention can also be combined with a customary perfume auxiliary adjuvants such as natural oils, synthetic oils, aldehydes, ketones, carboxylic acid esters, aryl alcohols, alkanols, lactones, saturated hydrocarbons, unsaturated hydrocarbons, fixatives, solvents, dispersants, surface active agents, aerosol propellants and the like.

The following examples serve to illustrate embodiments of our invention as it is now preferred to practice it. It will be understood that these examples are illustrative, and the invention is to be considered restrictive thereto only as indicated in the appended claims.

EXAMPLE I

Into a 5 liter reaction flask equipped with stirrer, reflux condenser, thermometer and addition funnel, the following materials are added:

| | |
|---|---|
| Myrcene | 1308 g (6.98 moles) |
| Formalin (37% formaldehyde) | 652 g (8.04 moles) |
| Propionaldehyde (97.5%) | 464 g (7.80 moles) |

Diethyl amine (58 g/0.795 moles) is added to the reaction mass with external cooling, as needed, to keep the temperature below 25°C.

50% wt/wt sulfuric acid (80 g/0.392 moles) is added to the reaction mass with external cooling, as needed, to maintain the temperature below 25°C. The pH of the reaction mass at this point is betwee 5 and 6.

The above-formed reaction mass is charged to a one gallon high pressure autoclave. The autoclave is sealed and operated at 150°C and 130 psig pressure for 3 hours.

The reaction mass from the autoclave is then added to a 5 liter reaction flask, and 500 g of 10% aqueous sodium carbonate is added with stirring. The mixture is then refluxed for 3 hours, after which it is cooled to 20°–25°C. The aqueous layer is removed and 750 ml toluene is added to the organic layer. The organic layer is washed successively with one 200 ml portion of 5% sulfuric acid, one 200 ml portion of water, one 200 ml portion of 10% sodium carbonate solution and two 200 ml portions of water. The toluene is then stripped on a rotary evaporator and the resulting product is distilled rapidly at 3 mm Hg pressure, using a 2-inch column. The resulting material is fractionated using an 18-inch Goodloe packed column at a vapor temperature of 101°–103°C and a pressure of 1.0 mm Hg. (Yield: 66.0% of theory). Infra-red, nuclear magnetic resonance and mass spectral analysis yield the information that the product has the structure:

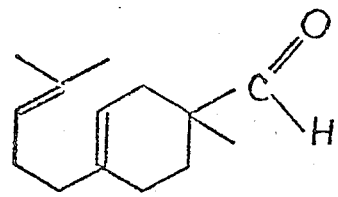

and

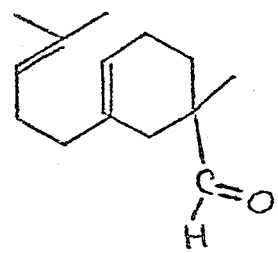

EXAMPLE II

A procedure is carried out in accordance with Example I, except that the autoclave is operated over a period of 5 hours rather than the 3 hour period indicated in Example I. The resulting yield is 69.8% of theory.

EXAMPLE III

The procedure is carried out in accordance with the process of Example I, scaled up so that 70 moles of myrcene is used and dimethyl amine gas is used instead of diethyl amine. The autoclave is operated for a period of 5 hours at 150°C. The resulting chemical yield is 80.0%.

EXAMPLE IV

A process is carried out in accordance with the process of Example I except that the autoclave reaction is carried out for a period of 5 hours at 180°C. The resulting chemical yield is 67.4%.

EXAMPLE V

A process according to Example I is carried out except that instead of using diethyl amine, dimethyl amine is used as a catalyst, and the reaction is carried out in the autoclave for a period of 5 hours at 180°C. The resultant chemical yield is 69%.

EXAMPLE VI

Into a 5 liter reaction flask equipped with stirrer, reflux condenser, thermometer and addition funnel, the following materials are added:

| | |
|---|---|
| Myrcene (72.6%) | 1,308 g (6.98 moles) |
| Acetone | 464 g (8.00 moles) |
| Formalin (37%) | 652 g (8.04 moles) |

The contents of the reaction vessel are cooled to 10°C, and 58 g (0.795 moles) of diethyl amine are added with external cooling, as needed, to keep the temperature of the reaction mass below 25°C. 80 g of 50% wt/wt sulfuric acid (0.392 moles of sulfuric acid) is added to the reaction mass with external cooling, as needed, to maintain the temperature below 25°C. The reaction mass is then charged to a one gallon autoclave, and the autoclave is sealed. The contents of the autoclave are heated, with stirring at 150°C and 150 psig pressure for a period of 5 hours. Toluene (100 ml) is added to the reaction mass from the autoclave, and the material is washed successively as follows:
  i. one 1 liter portion of water;
  ii. one 500 ml portion of 10% sulfuric acid;
  iii. one 500 ml portion of water;
  iv. one 500 ml portion of water;
  v. one 500 ml portion of 5% sodium bicarbonate;
  vi. one 1 liter portion of water The solvent is stripped off and the residue is distilled rapidly at a vapor temperature of 128°–129°C and a pressure of 2.0–2.1 mm Hg to give a product having the structure:

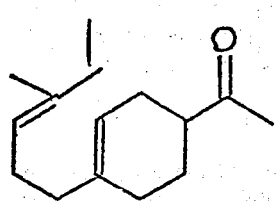

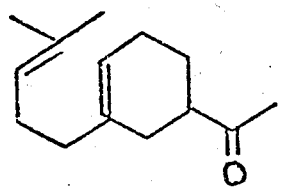

and

EXAMPLE VII

Into a 3 liter reaction flask equipped with stirrer, thermometer and reflux condenser, the following materials are added:

| | |
|---|---|
| Diethyl amine | 37 g |
| Toluene | 250 g |

While maintaining the temperature at 30°C, 52 g of 50% wt/wt sulfuric acid is added. 1,410 g of 77% myrcene and 580 g of acetone are then added to the reaction mass. The resulting reaction mixture is then transferred to a 1 gallon autoclave and 158 g of paraformaldehyde (95%) is added thereto. The autoclave is sealed and the contents stirred at 160°C for a period of 5 hours. The resulting reaction product is then added to a 5 liter reaction vessel, to which 1 liter of toluene is added. The aqueous layer is drained off and the organic layer is washed successively as follows:
  i. one 500 ml portion of 5% sulfuric acid;
  ii. one 500 ml portion of water;
  iii. one 500 ml portion of 5% sodium bicarbonate;

500 ml of toluene is added to the reaction mass which is then stripped and rapidly distilled at a vapor temperature of 174°–182°C and a pressure of 2.9–3.0 mm Hg. The structure of the resulting product is the same as that obtained in Example VI.

EXAMPLE VIII

To a solution of 1,308 g of myrcene (72.6%) 352 g of acetaldehyde and 546 g of methyl-ethyl ketone is added 240 g of an aqueous solution containing 72 g of diethyl amine and 99 g of concentrated sulfuric acid and 1 g of additional diethyl amine. The reaction mass is charged to an autoclave, and the autoclave is sealed and stirred for a period of 5 hours at 150°C and 75–120 psig pressure. At the end of this period of time the autoclave contents are emptied and 100 cc of toluene are added to the reaction mass. The reaction mass is then successively washed as follows:
  i. one 1 liter portion of water;
  ii. one 1 liter portion of water;
  iii. one 500 cc portion of 5% sodium bicarbonate solution;
  iv. one 500 cc portion of water 100 cc of toluene are added and the material is distilled rapidly at a vapor temperature of 124°–161°C and a pressure of 1.5–2 mm Hg. Distillation at a vapor temperature of 110°–150°C and a pressure of 2.0–2.5 mm Hg gives a product consisting of a mixture of the structures:

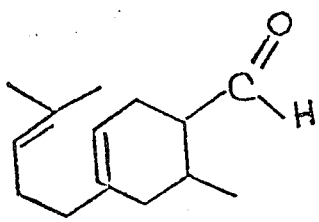
,
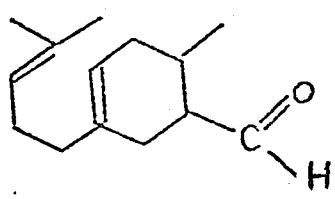

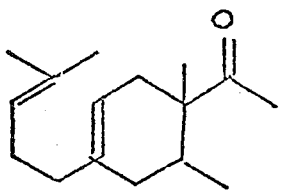
and
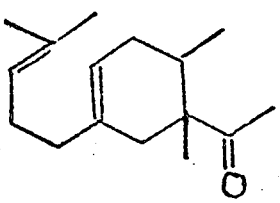

as confirmed by GLC, NMR, IR and mass spectral analysis.

EXAMPLE IX

Into a 5 reaction flask equipped with stirrer, reflux condenser, tHermometer and addition funnel, the following materials are added:

| | |
|---|---|
| Myrcene (77%) | 1,235 g (7.0 moles) |
| Formalin (37% formaldehyde) | 495 g (6.1 moles) |
| Methyl Ethyl Ketone | 432 g (6.0 moles) |

Diethyl amine (43 g/0.603 moles) is added to the reaction mass with external cooling, as needed, to keep the temperature below 25°C.

50% wt/wt sulfuric acid (62 g/0.605 moles) is added to the reaction mass with external cooling, as needed, to maintain the temperature below 25°C. The pH of the reaction mass at this point is between 5 and 6. The above-formed reaction mass is charged to a one gallon high pressure autoclave. The autoclave is sealed and operated at 160°C for a period of 6 hours.

The reaction mass now exists in two phases. The aqueous phase is separated from the organic phase, and the aqueous phase is extracted with one 200 cc portion of toluene. The toluene extract and the organic phase are combined and washed as follows:
i. one 500 cc portion of 50% phosphoric acid;
ii. one 500 cc portion of water;
iii. one 500 cc portion of 10% sodium carbonate;
iv. one 500 cc portion of water;
v. one 500 cc portion of saturated sodium chloride The reaction mass is then stripped of toluene solvent and distilled rapidly at a vapor temperature of 143°–178°C and a pressure of 3.0–4.5 mm Hg. The crude product is then fractionated on a Goodloe column at a vapor temperature of 120°–127°C and a pressure of 2.2–2.5 mm Hg, yielding a product which is a mixture of chemical compounds having the structures:

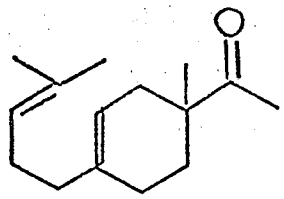
and
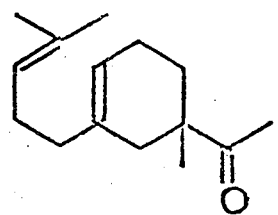

These structures are confirmed by GLC, mass spectral analysis, NMR analysis and infra-red analysis. The resulting material has an excellent peach-like aroma.

EXAMPLE X

Into a reaction flask, with stirring and cooling, the following materials are added:

| | |
|---|---|
| Formalin (37%) | 850 g (10.5 moles) |
| Diethyl amine | 73 g (1.0 moles) |
| Sulfuric acid (50%) | 102 g (0.5 moles) |

550 g (9.5 moles) of propionaldehyde, 660 g of dicyclopentadiene and 100 g of toluene are then added to the reaction mass. The contents of the reaction mass are then added to an autoclave, and the autoclave is sealed. The autoclave is operated for a period of 7.5 hours at 165°C and 50–55 psig pressure. At the end of this period of time, the autoclave contents are emptied into a flask and combined with one liter of toluene. The aqueous phase is separated and extracted with one 200 cc portion of toluene, and the toluene and organic layers are combined and washed as follows:
i. one 250 cc portion of 5% sulfuric acid;
ii. two 250 cc portions of water;
iii. one 250 cc portion of 5% sodium bicarbonate solution
iv. one 250 cc portion of saturated sodium chloride solution.

The crude material from several runs made in this way was distilled at 46°–53°C and 2.6–3.1 mm Hg. to give a product having the structure:

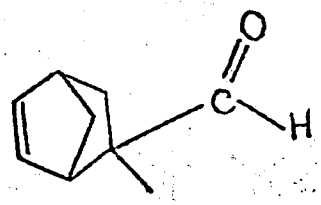

as confirmed by NMR, IR and mass spectral analysis.

EXAMPLE XI

Into a 5 liter reaction flask equipped with stirrer, reflux condenser, thermometer and addition funnel, the following materials are added:

| | |
|---|---|
| Allo-ocimene (91.3%) | 1,200 g (8 moles) |
| Formalin (37%) | 568 g (7 moles) |
| Acetone | 464 g (8 moles) |

The mixture is cooled, as needed, to maintain the temperature below 30°C while 58 g (0.795 moles) of di-

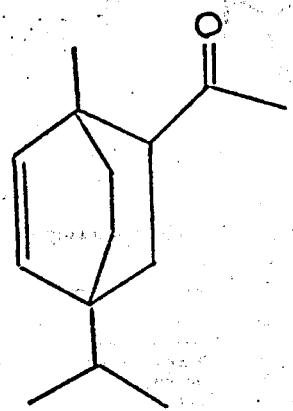

ethyl amine and 81 g of 50% wt/wt sulfuric acid are added successively. The reaction mass is then added to a one gallon autoclave, and the autoclave is sealed. The autoclave is operated for a period of 5 hours at a temperature of 150°C and 50–150 psig pressure. After this period of time, the autoclave is opened, and the aqueous phase is extracted with 250 cc of toluene and the organic phase and toluene extract are combined and washed as follows:
  i. one 250 cc portion of 55 sulfuric acid;
  ii. two 500 cc portions of 10% sodium chloride;
  iii. one 250 cc saturated sodium chloride solution
The reaction mass is stripped of toluene and rapidly distilled at 98°–128°C and a pressure of 3.7–4.2 mm Hg. The resulting product is a mixture of compounds having the structure:

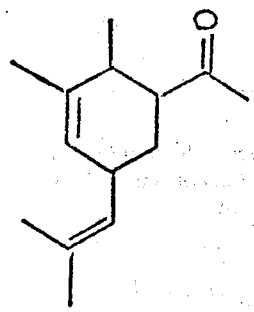 and 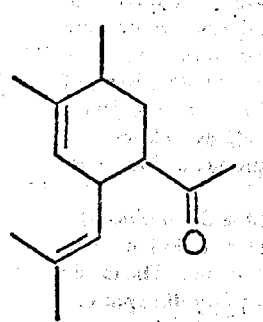

as confirmed by GLC, NMR and IR analysis.

EXAMPLE XII

Into a one gallon autoclave the following materials are placed:

| | |
|---|---|
| Alpha-terpinene | 800 g |
| Formalin (37%) | 584 g |
| Acetone | 557 g |
| Diethyl amine | 53 g |
| 50% Sulfuric acid | 75 g |

The autoclave is sealed and the reaction mass is heated to 150°C and maintained at that temperature for a period of 5 hours. At the end of that period of time the autoclave is opened and the reaction mass is removed. The aqueous phase is separated from the organic phase, and the organic phase is washed with one 200 ml portion of 5% phosphoric acid, and then one 200 ml portion of water. The reaction product is rush-over and fractionally distilled to yield a product having an intense woody aroma, having a structure confirmed by NMR, IR and mass spectral analysis to be:

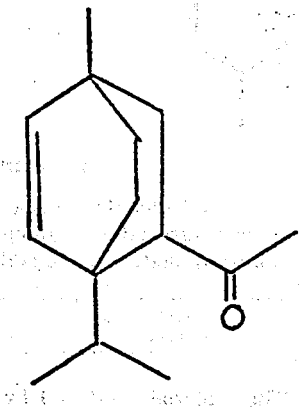

EXAMPLE XIII

Into a 5 liter reaction flask equipped with stirrer, reflux condenser, thermometer and addition funnel, the following materials are added:

| | |
|---|---|
| Allo-ocimene (91.3% | 1,200 g (8.0 moles) |
| Formalin (37%) | 568 g (7 moles) |
| Propionaldehyde | 406 g (7 moles) |

The mixture is cooled, as needed, to hold the temperature below 30°C and 58 g (0.795 moles) of diethyl amine and 81 g of 50% wt/wt sulfuric acid are added successively. The reaction mass is then charged to a 1 gallon autoclave and then stirred at 120°C for 2 hours and at 150°C for 3 hours. At the end of this period of time the reaction mass is removed from the autoclave and the aqueous phase is extracted with one 250 cc portion of toluene. The organic phase and the toluene extract are combined and washed as follows:
  i. one 500 ml portion of 10% sulfuric acid;
  ii. one 500 ml portion of water;
  iii. one 500 ml portion of 10% sodium chloride;
  iv. one 500 ml portion of saturated sodium chloride 5g of calcium carbonate is added to the resulting product, and the reaction mass is stripped of toluene and rapidly distilled at 92°–114°C and 3 mm Hg pressure. The crude product was fractionated using a 12-inch Goodloe column at 107°–111°C vapor temperature and 2.0–2.3 mm Hg pressure. The resultant product, as confirmed by NMR, IR and mass spectral analysis is a mixture of materials having the following structures:

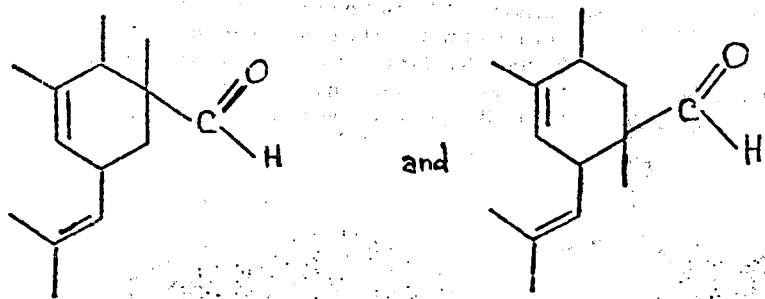

EXAMPLE XIV

Into a 3 liter three-neck flask equipped with stirrer, temperature, addition funnel, and reflux condenser, the following materials are added:

| Phosphoric acid (85%) | 500 g |
| Toluene | 500 ml |

The material produced by the process of Example I having the structure:

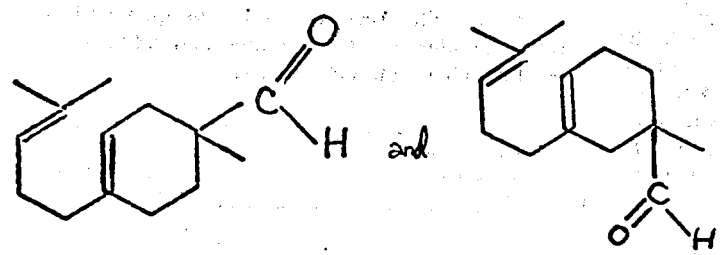

is added to the reaction mass, dropwise, over a period of 1.5 hours wih cooling as needed in order to maintain the temperature of the reaction mass at 50°–55°C. The reaction mass is maintained at 50°–55°C with stirring for a period of 3 hours. The reaction mass is then cooled to 20°–25°C and 500 ml of water is added. The reaction mass now exists in two phases: an organic phase and an aqueous phase. The two phases are separated and the aqueous phase is extracted with 250 ml of toluene. The toluene extracted and the organic phase are combined and washed successively as follows:
  i. two 250 ml portion of 10% aqueous sodium carbonate;
  ii. one 250 ml portion of saturated sodium chloride.

The solvent is stripped off and the reaction mass is rushed over at 200°C and 3 mm Hg pressure. The crude product is then distilled on an 18-inch Goodloe packed column to give the desired product having the structure:

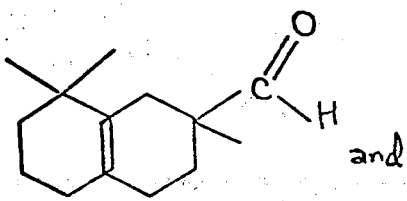

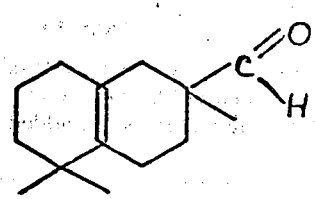

EXAMPLE XV

The following formulation is prepared:

| Ingredient | FLORAL MUGUET Parts by Weight |
|---|---|
| Benzyl Acetate | 150 |
| Geraniol | 100 |
| Citronellol | 80 |
| p-t-butylphenyl propionaldehyde | 100 |
| Hydroxy citronellal | 100 |
| Coumarin | 10 |
| Vanillin | 5 |
| n-undecanal | 1 |
| Phenyl Ethyl Alcohol | 100 |
| Beta-Ionone | 50 |
| Alpha-Methyl Ionone | 50 |
| Cinnamic Alcohol | 10 |
| Indole (10% in diethyl phthalate) | 5 |
| p-Hexyl Cinnamic Aldehyde | 50 |
| Linalool | 40 |
| Linalyl Acetate | 20 |
| Vetivert Bourbon | 4 |
| Bergamot Rectified | 20 |

Addition to this floral muguet formulation of 105 parts of the product produced according to Example I imparts to it a floral melony note.

Example XVI

The following formulation is prepared:

| FLORAL MUGUET | |
|---|---|
| Ingredient | Parts by Weight |
| Benzyl Acetate | 150 |
| Geraniol | 100 |
| Citronellol | 80 |
| p-t-butylphenyl propionaldehyde | 100 |
| Hydroxy Citronellal | 100 |
| Coumarin | 10 |
| Vanillin | 5 |
| n-undecanal | 1 |
| Phenyl Ethyl Alcohol | 100 |
| Beta-Ionone | 50 |
| Alpha-Methyl Ionone | 50 |
| Cinnamic Alcohol | 10 |
| Indole (10% in diethyl phthalate) | 5 |
| p-Hexyl Cinnamic Aldehyde | 50 |
| Linalool | 40 |
| Linalyl Acetate | 20 |
| Vetivert Bourbon | 4 |
| Bergamot Rectified | 20 |

Addition to the above formulation of 105 parts of the product produced according to Example XIV imparts to this formulation a floral melony note.

EXAMPLE XVII

The following formulation is prepared:

| FLORAL MUGUET | |
|---|---|
| Ingredients | Parts by Weight |
| Benzyl Acetate | 150 |
| Geraniol | 100 |
| Citronellol | 80 |
| p-t-butylphenyl propionaldehyde | 100 |
| Hydroxy citronellal | 100 |
| Coumarin | 10 |
| Vanillin | 10 |
| n-undecanal | 5 |
| Phenyl Ethyl Alcohol | 100 |
| Beta-Ionone | 50 |
| Alpha Methyl Ionone | 50 |
| Cinnamic Alcohol | 10 |
| Indole (10% in diethyl phthalate) | 5 |
| p-Hexyl Cinnamic Aldehyde) | 50 |
| Linalool | 40 |
| Linalyl Acetate | 20 |
| Vetivert Bourbon | 4 |
| Bergamot Rectified | 20 |

Addition to the above formulation of 105 parts of the product produced according to Example XII imparts to this floral muguet formulation a subtle woody note.

EXAMPLE XVIII

The following formulation is prepared:

| FLORAL MUGUET | |
|---|---|
| Ingredients | Parts by Weight |
| Benzyl Acetate | 150 |
| Geraniol | 100 |
| Citronellol | 80 |
| p-t-butylphenyl propionaldehyde | 100 |
| Hydroxy Citronellal | 100 |
| Coumarin | 10 |
| Vanillin | 5 |
| n-undecanal | 100 |
| Beta-Ionone | 50 |
| Alpha Methyl Ionone | 50 |
| Cinnamic Alcohol | 10 |
| Indole (10% in diethyl phthalate) | 5 |
| p-Hexyl Cinnamic Aldehyde | 50 |
| Linalool | 40 |
| Linalyl Acetate | 20 |
| Vetivert Bourbon | 4 |
| Bergamot Rectified | 20 |
| Benzyl Benzoate | 40 |

Addition to this floral muguet formulation of 65 parts of the product produced according to Example XV imparts to the formulation a green, woody, herbaceous note.

EXAMPLE XIX

The following formulation is prepared:

| FLORAL MUGUET | |
|---|---|
| Ingredients | Parts by Weight |
| Benzyl Acetate | 150 |
| Geraniol | 100 |
| Citronellol | 80 |
| p-t-butylphenyl propionaldehyde | 100 |
| Hydroxy Citronellal | 100 |
| Coumarin | 10 |
| Vanillin | 5 |
| n-undecanal | 1 |
| Phenyl Ethyl Alcohol | 100 |
| Beta-Ionone | 50 |
| Alpha-Methyl Ionone | 50 |
| Cinnamic Alcohol | 10 |
| Indole (10% in diethyl phthalate) | 5 |
| p-Hexyl Cinnamic Aldehyde | 50 |
| Linalool | 40 |
| Linalyl Acetate | 20 |
| Vetivert Bourbon | 4 |
| Bergamot Rectified | 20 |
| Benzyl Benzoate | 40 |

Addition to this floral muguet formulation of 65 parts of the product produced according to Example XIII imparts to the formulation a green, woody, herbaceous note.

EXAMPLE XX

Preparation of Soap Composition

One hundred grams of soap chips are mixed with one gram of the perfume composition of Example XV until a substantially homogeneous composition is obtained. The perfumed soap composition exhibits a floral muguet characteristic with a floral melony note.

EXAMPLE XXI

Preparation of a Detergent Composition

A total of 100 grams of a detergent powder is mixed with 0.15 grams of the perfume composition of Example XV until a substantially homogeneous composition is prepared. This composition exhibits a floral muguet fragrance, with a floral, melony note.

EXAMPLE XXII

Preparation of a Cosmetic Powder Composition

A cosmetic powder is prepared by mixing in a ball mill 100 grams of talcum powder with 0.25 grams of the product produced by the process of Example I. It has an excellent floral melony aroma.

EXAMPLE XXIII

Perfumed Liquid Detergent

Concentrated liquid detergent with a rich floral melony character are obtained containing 0.10%, 0.15% and 0.20% of the product produced by the process of Example I. They are prepared by adding and homogeneously mixing the appropriate quantity of the produce the process of Example I in the liquid detergent. The detergents all possess a floral melony fragrance, the intensity increasing with greater concentrations of the product produced by the process of Example I.

EXAMPLE XXIV

Cologne

The product produced by the process of Example I is incorporated in a cologne at a concentration of 2.5% in 85% ethanol; and into a handkerchief perfume at a concentration of 5% (in 95% aqueous ethanol). A distinct and definite floral melony fragrance is imparted to the cologne and to the handkerchief perfume.

EXAMPLE XXV

The composition of Example XVI is incorporated in a cologne at a concentration of 2.5% in 85% aqueous ethanol; and into a handkerchief perfume at a concentration of 20% (in 95% aqueous ethanol). The composition of Example XVI affords a distinct and definite strong floral muguet fragrance with a floral melony note to that handkerchief perfume and cologne.

EXAMPLE XXVI

Preparation of Soap Composition

One hundred grams of soap chips are mixed with 1 gram of the perfume composition of Example XVII until a substantially homogeneous composition is obtained. The perfumed soap composition exhibits a floral muguet characteristic with a woody note.

EXAMPLE XXVII

Preparation of a Detergent Composition

A total of 100 grams of a detergent powder is mixed with 0.15 grams of the perfume composition of Example XVII until a substantially homogeneous composition is prepared. This composition exhibits a floral muguet fragrance with a woody note.

EXAMPLE XXVIII

Preparation of a Cosmetic Powder Composition

A cosmetic powder is prepared by mixing in a ball mill 100 grams of talcum powder with 0.25 grams of the product produced by the process of Example XII. It has an excellent woody aroma.

EXAMPLE XXIX

Perfumed Liquid Detergent

Concentrated liquid detergent with a rich woody character are obtained containing 0.10, 0.15 and 0.20% of the product produced by the process of Example XII. They are prepared by adding and homogeneously mixing the appropriate quantity of the product produced by the process of Example XII in the liquid detergent. The detergents all possess a woody fragrance, the intensity increasing with greater concentrations of the product produced by the process of Example XII.

EXAMPLE XXX

Cologne

The product produced by the process of Example XII is incorporated in a cologne at a concentration of 2.5% in 85% aqueous ethanol; and into a handkerchief perfume at a concentration of 5% (in 95% aqueous ethanol). A distinct and definite woody fragrance is imparted to the cologne and to the handkerchief perfume.

EXAMPLE XXXI

The composition of Example XVII is incorporated in a cologne at a concentration of 2.5% in 85% aqueous ethanol; and into a handkerchief perfume at a concentration of 20% (in 95% aqueous ethanol). The composition of Example XVII affords a distinct and definite strong floral muguet fragrance (with a distinctive woody note) to that handkerchief perfume and cologne.

EXAMPLE XXXII

Preparation of Soap Composition

One hundred grams of soap chips are mixed with 1 gram of the perfume composition of Example XVIII until a substantially homogeneous composition is obtained. The perfumed soap composition exhibits a floral muguet characteristic with a woody, green, herbaceous note.

EXAMPLE XXXIII

Preparation of a Detergent Composition

A total of 100 grams of a detergent powder is mixed with 0.15 grams of the perfume composition of Example XVIII until a substantially homogeneous composition is prepared. This composition exhibits a floral muguet fragrance with a woody, green, herbaceous note.

EXAMPLE XXXIV

Preparation of a Cosmetic Powder Composition

A cosmetic powder is prepared by mixing in a ball mill 100 grams of talcum powder with 0.25 grams of the product produced by the process of Example XI. It has an excellent woody, green, herbaceous aroma.

EXAMPLE XXXV

Perfumed Liquid Detergent

Concentrated liquid detergent with a rich woody, green, herbaceous character are obtained containing 0.10%, 0.15% and 0.20% of the product produced according to the process of Example XIII. They are prepared by adding and homogeneously mixing the appropriate quantity of the product of Example XI in the liquid detergent. The detergents all possess a woody, green, herbaceous fragrance, the intensity increasing with greater concentrations of the product of the process of Example XI.

EXAMPLE XXXVI

Cologne

The product produced by the process of Example XI is incorporated in a cologne at a concentration of 2.5% in 85% aqueous ethanol; and into a handkerchief perfume at a concentration of 5% (in 95% aqueous ethanol). A distinct and definite woody, green, herbaceous fragrance is imparted to the cologne and to the handkerchief perfume.

EXAMPLE XXXVII

The composition of Example XVIII is incorporated in a cologne at a concentration of 2.5% in 85% aqueous ethanol; and into a handkerchief perfume at a concentration of 20% (in 95% aqueous ethanol). The composition of Example XVIII affords a distinct and definite strong floral muguet fragrance (with a distinctive woody, green, herbaceous note) to that handkerchief perfume and cologne.

EXAMPLE XXXVIII

Preparation of Soap Composition

One hundred grams of soap chips are mixed with 1 gram of the perfume composition of Example XIX until a substantially homogeneous composition is obtained. The perfumed soap composition exhibits a floral muguet characteristic with a woody, green, herbaceous note.

EXAMPLE XXXIX

Preparation of a Detergent Composition

A total of 100 grams of a detergent powder is mixed with 0.15 grams of the perfume composition of Example XIX until a substantially homogeneous composition is prepared. This composition exhibits a floral muguet fragrance with a woody, green, herbaceous note.

EXAMPLE XL

Preparation of a Cosmetic Powder Composition

A cosmetic powder is prepared by mixing in a ball mill 100 grams of talcum powder with 0.25 grams of the product produced by the process of Example XIII. It has an excellent woody, green, herbaceous aroma.

EXAMPLE XLI

Perfumed Liquid Detergent

Concentrated liquid detergent with a rich woody, green, herbaceous character are obtained containing 0.10, 0.15 and 0.20% of the product produced according to the process of Example XIII. They are prepared by adding and homogeneously mixing the appropriate quantity of the product of Example XIII in the liquid detergent. The detergents all possess a woody, green, herbaceous fragrance, the intensity increasing with greater concentrations of the product of the process of Example XIII.

EXAMPLE XLII

Cologne

The product produced by the process of Example XIII is incorporated in a cologne at a concentration of 2.5% in 85% aqueous ethanol; and into a handkerchief perfume at a concentration of 5% (in 95% aqueous ethanol). A distinct and definite woody, green, herbaceous fragrance is imparted to the cologne and to the handkerchief perfume.

EXAMPLE XLIII

The composition of Example XIX is incorporated in a cologne at a concentration of 2.5% in 85% aqueous ethanol; and into a handkerchief perfume at a concentration of 20% (in 95% aqueous ethanol). The composition of Example XIX affords a distinct and definite strong floral muguet fragrance (with a distinctive woody, green, herbaceous note).

What is claimed is:

1. A composition consisting essentially of a mixture of chemical compounds having the structures:

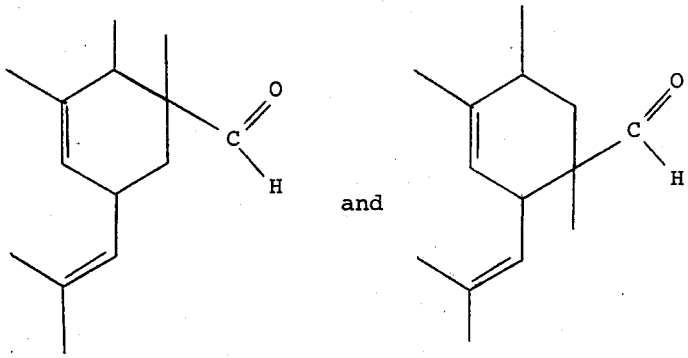

UNITED STATES PATENT AND TRADEMARK OFFICE
CERTIFICATE OF CORRECTION

PATENT NO. : 3,981,924
DATED : September 21, 1976
INVENTOR(S) : JOHN B. HALL

It is certified that error appears in the above-identified patent and that said Letters Patent are hereby corrected as shown below:

Column 2, Line 14: delete "carbonyl"

Column 5, Line 33: change "inpurities" to read --- in purities ---

Column 9, last formula: Replace the formula:

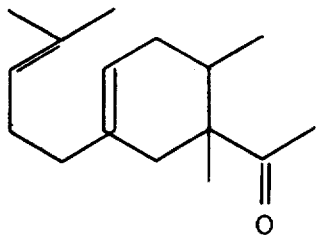

with the following formula:

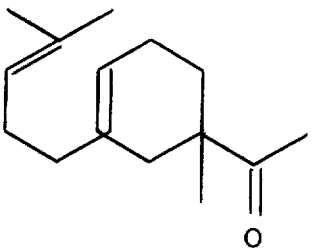

Column 16, Line 13: change "betwee" to read --- between ---

UNITED STATES PATENT AND TRADEMARK OFFICE
CERTIFICATE OF CORRECTION

PATENT NO. : 3,981,924
DATED : September 21, 1976
INVENTOR(S) : JOHN B. HALL

It is certified that error appears in the above-identified patent and that said Letters Patent are hereby corrected as shown below:

Column 17, Last line: Replace the formula:

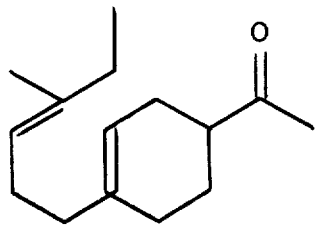

with the following formula:

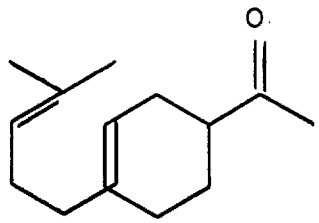

Column 19, Line 26: replace "tHermometer" with ---thermometer---.

Column 22, Line 21: replace "rush-over" with --- rushed-over ---

Signed and Sealed this

Eighth Day of February 1977

[SEAL]

Attest:

RUTH C. MASON
Attesting Officer

C. MARSHALL DANN
Commissioner of Patents and Trademarks